United States Patent
Lerg et al.

(10) Patent No.: US 10,213,371 B2
(45) Date of Patent: Feb. 26, 2019

(54) STABLE COSMETIC PREPARATION WITH A HIGH PIGMENT CONTENT

(75) Inventors: Heike Lerg, Hamburg (DE); Manuela Koehler, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 13/459,662

(22) Filed: Apr. 30, 2012

(65) Prior Publication Data

US 2013/0266621 A1 Oct. 10, 2013

(30) Foreign Application Priority Data

Apr. 4, 2012 (DE) .................. 10 2012 205 526

(51) Int. Cl.
| | |
|---|---|
| *A61K 8/06* | (2006.01) |
| *A61K 8/27* | (2006.01) |
| *A61K 8/29* | (2006.01) |
| *A61K 8/40* | (2006.01) |
| *A61Q 17/04* | (2006.01) |

(52) U.S. Cl.
CPC ............... *A61K 8/27* (2013.01); *A61K 8/062* (2013.01); *A61K 8/29* (2013.01); *A61K 8/40* (2013.01); *A61Q 17/04* (2013.01)

(58) Field of Classification Search
CPC . A61K 8/27; A61K 8/29; A61K 8/062; A61K 8/40; A61Q 17/04
USPC ............................................... 424/401
See application file for complete search history.

(56) References Cited

U.S. PATENT DOCUMENTS

| | | | | |
|---|---|---|---|---|
| 2004/0096470 | A1* | 5/2004 | Tanaka et al. | ............... 424/401 |
| 2005/0196360 | A1* | 9/2005 | Comte | ................. A61K 8/29 424/59 |
| 2009/0041847 | A1* | 2/2009 | Bonda et al. | ................ 424/489 |
| 2009/0324570 | A1 | 12/2009 | Bonda et al. | |
| 2011/0110988 | A1* | 5/2011 | Susak et al. | ................ 424/401 |
| 2011/0251242 | A1 | 10/2011 | Bonda et al. | |
| 2012/0269744 | A1* | 10/2012 | Spaulding et al. | ............. 424/59 |
| 2013/0136701 | A1* | 5/2013 | Kasai | .................... A61Q 17/04 424/43 |

FOREIGN PATENT DOCUMENTS

WO 2009020676 A1 2/2009

* cited by examiner

*Primary Examiner* — Nannette Holloman
(74) *Attorney, Agent, or Firm* — Abel Law Group, LLP

(57) ABSTRACT

A cosmetic preparation comprising ethylhexyl methoxycrylene and at least 20% by weight, based on the total weight of the preparation, of titanium dioxide and/or zinc oxide.

20 Claims, 4 Drawing Sheets

A

B c

A

B

C

STABLE COSMETIC PREPARATION WITH A HIGH PIGMENT CONTENT

CROSS-REFERENCE TO RELATED APPLICATIONS

The present application claims priority under 35 U.S.C. § 119 of German Patent Application No. 10 2012 205 526.6, filed on Apr. 4, 2012, the disclosure of which is expressly incorporated by reference herein in its entirety.

BACKGROUND OF THE INVENTION

1. Field of the Invention

The present invention relates to a cosmetic preparation comprising ethylhexyl methoxycrylene and particulate inorganic photoprotective filter pigments.

2. Discussion of Background Information

The trend away from genteel pallor towards "healthy, sporty brown skin" has been unbroken for years. In order to achieve this, people subject their skin to solar radiation since this causes pigment formation in the sense of melanin formation. However, the ultraviolet radiation of sunlight also has a harmful effect on the skin. Besides the acute damage (sunburn), long term damage such as an increased risk of suffering from skin cancer, arises with excessive irradiation with light from the UVB range (wavelength: 280-320 nm). Moreover, the effect of too much UVB and UVA radiation (wavelength: 320-400 nm) is a weakening of the elastic and collagenous fibers of connective tissue. This leads to numerous phototoxic and photoallergic reactions, resulting in premature skin aging.

To protect the skin, a series of photoprotective filter substances has therefore been developed which can be used in cosmetic preparations. These UVA and UVB filters are summarized in most industrialized countries in the form of positive lists such as Annex 7 of the German Cosmetics Ordinance.

A particular form of UV photoprotective filter substances are the micropigments. The UV protective effect of the micropigments is based on the physical effects of reflection and light scattering. In cosmetic preparations, the micropigments used are almost exclusively inorganic micropigments made of titanium dioxide, zinc oxide or mixed oxides with, for example, iron oxides.

The advantages of micropigments as UV filter substance in cosmetic preparations are primarily that the pigments do not penetrate into the skin, in contrast to those which are present in dissolved or liquid form. The occurrence of allergic reactions is therefore excluded.

However, a disadvantage in the prior art is the fact that inorganic micropigments, particularly in relatively high concentrations, can only be incorporated into cosmetic preparations with poor stability. If the micropigments are provided with dispersion auxiliaries, moreover, the emulsifier system changes. The storage stability is then reduced. In this connection, oil-in-water emulsions (O/W emulsions) are particularly unstable.

Moreover, inorganic micropigments such as titanium dioxide and zinc oxide have the disadvantage of forming agglomerates in the preparation itself and also following application to the skin; these can be seen as unattractive, white residues. This phenomenon, called "whitening", is not only visually unattractive, but reduces and alters the reflection and scattering behavior of these UV filters, as a result of which the UV protection of the preparation suffers. Also, this problem increases as the concentration of inorganic micropigments in the preparation increases.

In view of the foregoing, it would be desirable to have available cosmetic preparations (in particular O/W emulsions) into which inorganic photoprotective filter pigments (in particular titanium dioxide and zinc oxide) can be stably incorporated. In addition, the formulations, when applied to the skin, should have an absorption spectrum that is stable over a prolonged use period with appropriate UVA protection (Europe in accordance with Colipa, USA in accordance with FDA, UK Boots Star Ratio etc).

SUMMARY OF THE INVENTION

The present invention provides a cosmetic preparation comprising
(a) ethylhexyl methoxycrylene (hereafter sometimes referred as "compound A") of formula

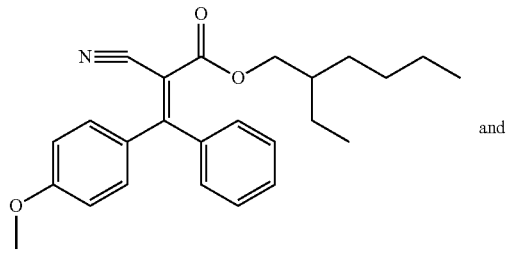 [SMILES: CCCCC(CC)COC(=O)/C(C#N)=C(\c1ccccc1)c1ccc(OC)cc1]

and (b) at least about 20% by weight, based on the total weight of the preparation, of titanium dioxide and/or zinc oxide.

In one aspect of the preparation, the preparation may be present in the form of an emulsion, e.g., in the form of an O/W emulsion.

In another aspect, the preparation may comprise one or more O/W emulsifiers selected from glyceryl stearate citrate, glyceryl stearate, cetearyl glucosides, stearic acid and salts thereof, polyglyceryl-3 methylglycose distearate, ceteareth-20, PEG-40 stearate, PEG-100 stearate, sodium cetearyl sulfate, cetearyl sulfosuccinate, sodium stearylglutamate, potassium cetylphosphate, and dimethyl dioctadecylammonium chloride and/or may comprise O/W emulsifiers in a total concentration of from about 0.001% to about 10% by weight, e.g., from about 0.1% to about 7% by weight, based on the total weight of the preparation.

In yet another aspect of the preparation of the present invention, the titanium dioxide and/or zinc oxide particles may have a primary particle size of less than about 300 nm, e.g., less than about 200 nm, or less than about 150 nm and/or the titanium dioxide and/or zinc oxide particles may be present in a total concentration of at least about 23%, e.g., at least about 25% by weight and not more than about 40% by weight, e.g., not more than about 35% by weight, or not more than about 30% by weight, based on the total weight of the preparation.

In a still further aspect of the preparation, compound A may be present in a total concentration of at least about 0.5%, e.g., at least about 1%, at least about 2%, or at least about 4% by weight and not more than about 10%, e.g., not more than about 8%, or not more than about 6% by weight, based on the total weight of the preparation.

In another aspect of the preparation, the preparation may further comprise one or more UV filters which are different from compound A. For example, the one or more UV filters may be present in total concentration of from about 0.5% to about 30% by weight, based on a total weight of the preparation.

In another aspect, the preparation may further comprise xanthan gum. For example, the xanthan gum may be present in a concentration of at least about 0.05% by weight, e.g., at least about 0.1%, at least about 0.2%, or at least about 0.4% by weight, and not more than about 1% by weight.

In yet another aspect, the preparation may further compriseone or more active ingredients selected from glycyrrhetic acid, urea, arctiin, alpha-lipoic acid, folic acid, phytoene, D-biotin, coenzyme Q10, alpha-glucosylrutin, carnitine, carnosine, caffeine, natural and/or synthetic isoflavonoids, glycerylglucose, creatine, creatinine, taurine, ß-alanine, and licochalcone A and/or may further comprise one or more of propylene glycol, butylene glycol, 2-methylpropane-1,3-diol, 1,2-pentanediol, 1,2-hexanediol, 1,2-octanediol, and 1,2-decanediol.

The present invention also provides a method of improving the dispersibility of particulate titanium dioxide and/or zinc oxide in a liquid cosmetic preparation which comprises an oil phase. The method comprises incorporating into the preparation a compound of formula:

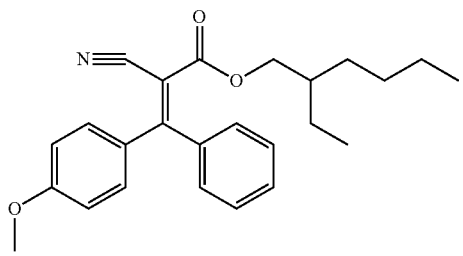 [SMILES: CCCCC(CC)COC(=O)/C(C#N)=C(\c1ccccc1)c1ccc(OC)cc1]

in an amount that is sufficient to improve the dispersibility of titanium dioxide and/or zinc oxide in the preparation.

In one aspect of the method, the titanium dioxide and/or zinc oxide may be incorporated in a total concentration of at least about 20% by weight, based on the total weight of the preparation.

BRIEF DESCRIPTION OF THE DRAWINGS

The present invention is further described in the detailed description which follows, in reference to the drawings by way of non-limiting examples of exemplary embodiments of the present invention, and wherein.

DETAILED DESCRIPTION OF THE PRESENT INVENTION

Figure 1A:
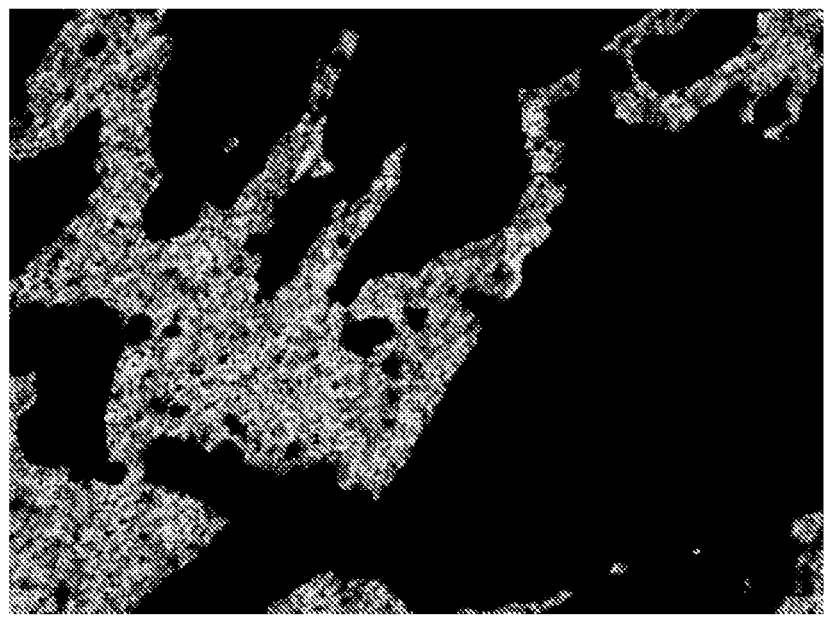
FIG. 1a and FIG. 1b are microphotographs of a composition according to the invention and two comparative compositions, showing titanium dioxide particles dispersed in the preparation.
Figure 1A:
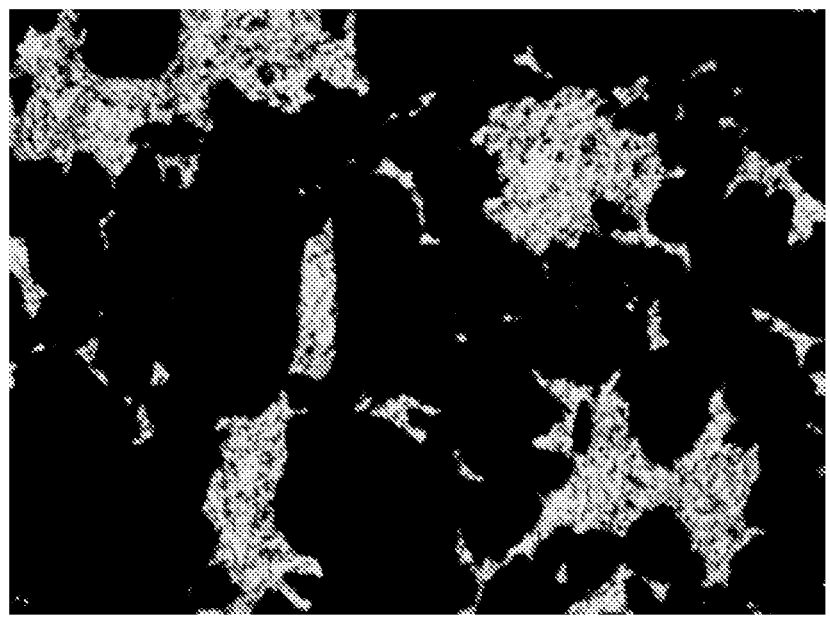

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Compound A is commercially available from, e.g., Hallstar under the tradename Solastay S1. It is also mentioned in, e.g., US 2009/0324570, US 2011/0251242 and WO 2009/020676, the entire disclosures of which are incorporated by reference herein.

It has unexpectedly been found that compared to the related octocrylene or the often used $C_{12}$-$C_{15}$ alkylbenzoate, ethylhexyl methoxycrylene results in a considerably more uniform distribution of titanium dioxide and/or zinc oxide particles in an oil phase. Moreover, the use of ethylhexyl methoxycrylene leads to the preparations losing oil to a significantly lesser extent compared to the use of octocrylene or $C_{12}$-$C_{15}$ alkylbenzoate. Last but not least, the use of ethylhexyl methoxycrylene, when compared with octocrylene or $C_{12}$-$C_{15}$ alkylbenzoate, leads to emulsions becoming more homogeneous (see comparative results below).

According to the invention, it is advantageous if the preparation is in the form of an emulsion, preferably an O/W emulsion.

Preferred O/W emulsifiers for use in the emulsion include glyceryl stearate citrate, glyceryl stearate, cetearyl glucoside, stearic acid and salts thereof, polyglyceryl-3 methylglucose distearate, ceteareth-20, PEG-40 stearate, PEG-100 stearate, sodium cetearyl sulfate, cetearyl sulfosuccinate, sodium stearylglutamate, potassium cetylphosphate, dimethyldioctadecylammonium chloride, and polyglyceryl-10 stearate.

In advantageous embodiments the preparation of the present invention comprises O/W emulsifiers in a total concentration of from about 0.001% to about 10% by weight and preferably in a concentration of from about 0.1% to about 7% by weight, based on the total weight of the preparation.

It further is advantageous for the titanium dioxide and/or zinc oxide particles to have a primary particle size of less than about 300 nm, e.g., less than about 200 nm, or less than about 150 nm.

According to the invention, it is also advantageous for the titanium dioxide and/or zinc oxide particles to be surface-coated. The surface coating may comprise providing the metal oxide particles with a thin hydrophilic or hydrophobic inorganic or organic layer by methods known per se. According to the present invention the different surface coatings can also comprise water. As a result of the surface treatment, the metal oxide is given a hydrophilic, amphiphilic or hydrophobic character.

Examples of inorganic surface coatings which are suitable for the purposes of the instant invention comprise aluminum oxide ($Al_2O_3$), aluminum hydroxide $Al(OH)_3$, aluminum oxide hydrate (also: Alumina, CAS-No.: 1333-84-2), sodium hexametaphosphate $(NaPO_3)_6$, sodium metaphosphate $(NaPO_3)_n$, silicon dioxide ($SiO_2$) (also: Silica, CAS-No.: 7631-86-9), and iron oxide ($Fe_2O_3$). These inorganic surface coatings can be present on their own, in combination and/or in combination with organic coating materials.

Examples of organic surface coatings which are suitable for use in the present invention include vegetable or animal aluminum stearate, vegetable or animal stearic acid, lauric acid, dime-thylpolysiloxane (also: dimethicone), methylpolysiloxane (methicone), simethicone (a mixture of di-methylpolysiloxane with an average chain length of about 200 to about 350 dimethylsiloxane units and silica gel), and octyltrimethylsilane. These organic surface coatings can be present on their own, in combination and/or in combination with inorganic coating materials.

Zinc oxide particles for use according to the present invention and predispersions of zinc oxide particles are available for example under the following trade names:

| Trade Name | Coating | Manufacturer |
|---|---|---|
| Z- Cote HP1 | 2% Dimethicone | BASF |
| Z- Cote | / | BASF |
| ZnO NDM | 5% Dimethicone | Haarmann &Reimer |
| MZ- 505S | 5% Methicone | Tayca Corporation |

Zinc oxides that are particularly preferred according to the present invention are not surface-treated, such as, for example, the products with the trade name Z-Cote (BASF) or Zinkoxid Neutral (Haarmann & Reimer), or carry a surface coating made of methicone and/or dimethicone, as is present, for example, in the products with the trade names Z-Cote HP1 (BASF), Zinkoxid NDM (Haarmann & Reimer), MZ-303M, MZ-505M, MZ-707M, MZ-5055, MZ-7075 (Tayca).

Advantageous titanium dioxides for use in the instant invention include the following products:

| Trade Name | Coating | Additional Constituents of Predispersion | Manufacturer |
|---|---|---|---|
| MT-100TV | Aluminum Hydroxide Stearic Acid | — | Tayca Corporation |
| MT-100Z | Aluminum Hydroxide Stearic Acid | — | Tayca Corporation |
| MT-100F | Stearic acid Iron Oxide | — | Tayca Corporation |
| MT-500SAS | Alumina, Silica Silicone | — | Tayca Corporation |
| MT-100AQ | Silica Aluminum Hydroxide Alginic Acid | — | Tayca Corporation |
| Eusolex T-2000 | Alumina Simethicone | — | Merck KgaA |
| Eusolex TS | Alumina, Stearic Acid | — | Merck KgaA |
| Eusolex T-AVO | Silica | — | Merck KgaA |
| Titandioxid P25 | None | — | Evonik |
| Titandioxid T805 (Uvinul TiO$_2$) | Octyltrimethylsilane | — | Evonik |
| UV-Titan X170 | Alumina Dimethicone | — | Kemira |
| UV-Titan X161 | Alumina, Silica Stearic Acid | — | Kemira |
| UV Titan M765 | Alumina Triethoxy Caprylsilane | | Sachtleben |
| MTY-600 BS | Methylhydrogenpolysiloxane | | Tayca |
| SOLAVEIL XT-300 | Stearic Acid + Alumina | Caprylic/Capric Triglyceride | Croda |
| EUSOLEX T, ARTNR 113911 | Simethicone | | Merck |
| Tioveil AQ 10PG | Alumina Silica | Water Propylenglycol | Solaveil Uniquema |
| Mirasun TiW 60 | Alumina Silica | Water | Rhodia |
| Titandioxid T-817 (Iron/Titanium Mixed Oxide) | Iron Oxide | | Evonik |

Particularly preferred titanium dioxides for use in the present invention include MT-100 Z and MT-100 TV from Tayca Corporation, Eusolex T-2000 and Eusolex T-AVO from Merck, titanium dioxide T 805 from Evonik, iron/titanium mixed oxide titanium dioxide T817 from Degussa, UV Titan M765 from Sachtleben, EUSOLEX T from Merck, and MTY 600 BS from Tayca.

According to the present invention it is advantageous if the preparation comprises compound A in a concentration of from about 0.5% to about 10% by weight, e.g., from about 2% to about 8%, based on the total weight of the preparation.

It further is advantageous for the preparation of the present invention to comprise one or more UV filters, in particular UV filters selected from 2-phenylbenzimidazole-5-sulfonic acid and salts thereof; phenylene-1,4-bis(2-benzimidazyl)-3,3,5,5'-tetrasulfonic acid salts; 1,4-di(2-oxo-10-sulfo-3-bornylidenemethyl)benzene and salts thereof; 4-(2-oxo-3-bornylidenemethyl)-benzenesulfonic acid salts; 2-methyl-5-(2-oxo-3-bornylidenemethyl)sulfonic acid salts; 2,2'-me-thylenebis(6-(2H-benzotriazol-2-yl)-4-(1,1,3,3-tetramethylbutyl)phenol); 2-(2H-benzotriazol-2-yl)-4-methyl-6-[2-methyl-3-[1,3,3,3-tetramethyl-1-[(trimethylsilyl)oxy]disiloxanyl]propyl]phenol; 3-(4-methylbenzylidene) camphor; 3-benzylidenecamphor; ethylhexyl salicylate; terephthalidenedicamphorsulfonic acid; 4-(tert-butyl)-4'-methoxydibenzoylmethane; 2-ethylhexyl 2-cyano-3,3-diphenylacrylate; 2-ethylhexyl 4-(dimethylamino)benzoate; amyl 4-(dimethylamino)benzoate; di(2-ethylhexyl) 4-methoxybenzalmalonate; 2-ethylhexyl 4-methoxycinnamate; isoamyl 4-methoxycinnamate; 2-hydroxy-4-methoxybenzophenone, 2-hydroxy-4-methoxy-4'-methylbenzophenone; 2,2'-dihydroxy-4-methoxybenzophenone; hexyl 2-(4'-diethylamino-2'-hydroxybenzoyl)benzoate; homomethyl salicylate; 2-ethylhexyl 2-hydroxybenzoate; dimethicodiethyl benzalmalonate; 3-(4-(2,2-bisethoxycarbonylvinyl) phenoxy)propenyl)methoxysiloxane/dimethylsiloxane copolymer; dioctylbutylamidotriazone (INCI: Diethylhexyl-Butamidotriazone); 2,4-bis[5-(dimethylpropyl)benzoxazol-2-yl-(4-phenyl)imino]-6-(2-ethylhexyl)imino-1,3,5-triazine with the CAS No. 288254-16-0; tris(2-ethylhexyl) 4,4',4"-(1,3,5-triazine-2,4,6-triyltriimino)trisbenzoate (also: 2,4,6-tris[anilino(p-carbo-2'-ethyl-1'-hexyloxy)]-1,3,5-triazine (INCI: Ethylhexyl Triazone); 2,4-bis{[4-(2-ethylhexyloxy)-2-hydroxy]phenyl}-6-(4-methoxyphenyl)-1,3,5-triazine; 2,4,6-tribiphenyl-4-yl-1,3,5-triazine; merocyanines.

The one or more UV filters may be present, for example, in a total concentration of from about 0.5% to about 30% by weight, e.g., from about 2% to about 25% by weight, based on the total weight of the preparation.

Of course, the preparations according to the invention may also comprise additional ingredients. For example, the water phase of the preparations may advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products, polymers, foam stabilizers, electrolytes, self-tanning agents such as dihydroxyacetone, and in particular one or more thickeners, which can be advantageously selected from silicon dioxide, aluminum silicates, polysaccharides and/or derivatives thereof, e.g. hyaluronic acid, xanthan gum, hydroxypropylmethylcellulose, particularly advantageously from polyacrylates, preferably a polyacrylate from the group of the so-called carbopols, for example carbopols of the grades 980, 981, 1382, 2984, 5984, in each case individually or in combination. In addition or instead of polymeric thickeners the preparation may also comprise siloxane elastomers. A particularly preferred thickener is xanthan gum.

The preparations according to the present invention further may advantageously comprise one or more humectants (moisturizers). Humectants (moisturizers) is the term used to refer to substances or substance mixtures which give cosmetic preparations the property, following application and/or spreading on the skin surface, of reducing the release of moisture by the horny layer (also called transepidermal water loss (TEWL)) and/or of positively influencing the hydration of the horny layer.

Non-limiting examples of advantageous humectants (moisturizers) for use in the instant invention include glycerol, lactic acid and/or lactates, in particular sodium lactate, butylene glycol, propylene glycol, biosaccharide gum-1, hydroxyethylurea, glycine soya, ethylhexyloxyglycerol, pyrrolidonecarboxylic acid, glycerylglucose quaternary compounds, alkanediols and urea. In addition, it is particularly advantageous to use polymeric moisturizers from the group of water-soluble and/or water-swellable and/or water-swellable polysaccharides. Of particular advantage are, for example, hyaluronic acid, chitosan and/or a fucose-rich polysaccharide, which is listed in the Chemical Abstracts under the registration number 178463-23-5 and is available, e.g. under the name Fucogel®1000 from SOLABIA S.A.

The cosmetic preparations of the instant invention may comprise one or more humectants in a total concentration of, for example, from about 0.1% to about 20% by weight, e.g., from about 0.5% to about 15% by weight, based on the total weight of the preparation. Often the preparations will comprise at least about 1%, e.g., at least about 2%, at least about 3%, at least about 4%, or at least about 5% by weight of one or more moisturizers. A preferred moisturizer for use in the present invention is glycerol.

The cosmetic preparations according to the invention may also comprise fillers which e.g. further improve the sensory and cosmetic properties of the formulations and, for example, to bring about or boost a velvety or silky skin feel. Within the context of the present invention, advantageous fillers include starch and starch derivatives (such as e.g. tapioca starch, distarch phosphate, polysilsesquioxanes, siloxane elastomers, aluminum and/or sodium starch octenylsuccinate and the like), pigments which have neither a primarily UV filter effect nor a coloring effect (such as e.g. boron nitride etc.), polyethylene, nylon, Aerosils® (CAS No. 7631-86-9) and/or talc. Preferred fillers for use in the instant invention include polyethylene, nylon, natural or modified starches such as tapioca starch and/or silicates such as, for example talc.

The oil phase of the formulations according to the invention may advantageously be selected from one or more polar oils, for example from lecithins and fatty acid triglycerides, namely the triglycerol esters of saturated and/or unsaturated, branched and/or unbranched alkanecarboxylic acids having a chain length of from 8 to 24, in particular 12 to 18 carbon atoms. The fatty acid triglycerides may advantageously be selected, for example, from synthetic, semisynthetic and natural oils, such as e.g. cocoglyceride, olive oil, sunflower oil, soya oil, peanut oil, rapeseed oil, argan oil, almond oil, palm oil, coconut oil, ricinus oil, wheatgerm oil, grapeseed oil, safflower oil, evening primrose oil, macadamia nut oil and the like.

Also advantageous for use in the oil phase are, e.g., natural waxes of animal and vegetable origin, such as, for example, beeswax and other insect waxes, and also berry wax, shea butter and/or lanolin (wool wax).

Further advantageous polar oil components include the esters of saturated and/or unsaturated, branched and/or unbranched alkanecarboxylic acids of chain length of from 3 to 30 carbon atoms and saturated and/or unsaturated, branched and/or unbranched alcohols having a chain length of from 3 to 30 carbon atoms, and also from esters of aromatic carboxylic acids and saturated and/or unsaturated, branched and/or unbranched alcohols having a chain length of from 3 to 30 carbon atoms. Such ester oils may advantageously be selected from octyl palmitate, octyl cocoate, octyl isostearate, octyldodeceyl myristate, octyldodecanol, cetearyl isononanoate, isopropyl myristate, iso-propyl palmitate, isopropyl stearate, isopropyl oleate, n-butyl stearate, n-hexyl laurate, n-decyl-oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and also synthetic, semisynthetic and natural mixtures of such esters, such as e.g. jojoba oil.

Furthermore, the oil phase may advantageously comprise dialkyl ethers and dialkyl carbonates, examples whereof include dicaprylyl ether (Cetiol OE) and/or dicaprylyl carbonate, for example that available under the trade name Cetiol CC from Cognis.

It also is possible to select the oil component or the oil components from isoeicosane, neo-pentyl glycol diheptanoate, propylene glycol dicaprylate/dicaprate, caprylic/capric/diglyceryl succi-nate, butylene glycol dicaprylate/dicaprate, cocoglycerides (e.g. Myritol® 331 from Henkel), $C_{12\text{-}13}$-alkyl lactate, di-$C_{12\text{-}13}$-alkyl tartrate, triisostearin, dipentaerythritylhexacaprylate/hexacaprate, propylene glycol monoisostearate, tricaprylin, dimethylisosorbide. It is particularly advantageous if the oil phase of the formulations according to the invention comprises $C_{12\text{-}15}$-alkylbenzoate or consists entirely thereof. Often the preparations of the present invention will comprise at least about 0.5% by weight, e.g., at least about 1%, or at least about 2% by weight, but usually not more than about 10%, e.g., not more than about 9%, or not more than about 8% by weight of $C_{12\text{-}15}$-alkylbenzoate, based on the total weight of the preparation.

Advantageous oil components also include butyloctyl salicylate (for example that available under the trade name Hallbrite BHB from CP Hall), hexadecyl benzoate and butyloctyl benzoate and mixtures thereof (Hallstar AB) and/or diethylhexyl naphthalate (Hallbrite TQ from CP Hall or Corapan®TQ from Haarmann & Reimer).

Within the context of the present invention, any desired mixtures of oil and wax components may, of course also be used advantageously.

In addition, the oil phase can likewise advantageously also comprise nonpolar oils, for example those which are selected from the group of the branched and unbranched hydrocarbons and hydrocarbon waxes, in particular mineral oil, vaseline (petrolatum), paraffin oil, squalane and squalene, polyolefins, hydrogenated polyisobutenes and isohexadecane. Polydecenes are the preferred substances among the polyolefins.

The oil phase can advantageously also comprise cyclic or linear silicone oils or consist entirely of such oils, although it is preferred to use additional oil phase components apart from the silicone oil or the silicone oils. Often the preparations according to the present invention will comprise a total of at least about 1%, e.g., at least about 2%, at least about 3%, or at least about 4% by weight, but usually not more than about 10%, e.g., not more than about 9%, or not more than about 8% by weight of one or more cyclic or linear silicone oils, based on the total weight of the preparation.

Silicone oils are high molecular weight synthetic polymeric compounds in which silicon atoms are linked via oxygen atoms in a chain-like and/or net-like manner and the remaining valences of the silicon are saturated by hydrocarbon radicals (in most cases methyl groups, more rarely ethyl, propyl, phenyl groups etc.). Systematically, the silicone oils are referred to as polyorganosiloxanes. The methyl-substituted polyorganosiloxanes, which are the most important compounds of this group in terms of amount and are characterized by the following structural formula

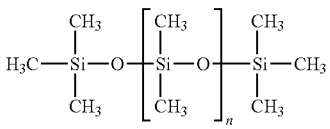

are also referred to as polydimethylsiloxane or dimethicone (INCI). Dimethicones come in different chain lengths and/or with different molecular weights.

Within the context of the present invention, particularly advantageous polyorganosiloxanes are, for example, dimethylpolysiloxanes [poly(dimethylsiloxane)], which are available, for example, under the trade names Abil 10 to 10 000 from Th. Goldschmidt. Also advantageous are phenyl-methylpolysiloxanes (INCI: Phenyl Dimethicone, Phenyl Trimethicone), cyclic silicones (octamethylcyclotetrasiloxane or decamethylcyclopentasiloxane), which are also referred to as cyclomethicones in accordance with INCI, amino-modified silicones (INCI: Amodimethicones) and silicone waxes, e.g. polysiloxane-polyalkylene copolymers (INCI: Stearyl Dimethicone and Cetyl Dimethicone) and dialkoxydimethylpolysiloxanes (Stearoxy Dimethicones and Behenoxy Stearyl Dimethicones), which are available as various Abil wax grades from Th. Goldschmidt Other silicone oils, however, can also be used advantageously for the purposes of the present invention, for example cetyldimethicone, hexamethylcyclotrisiloxane, polydimethylsiloxane, poly(methyl-phenylsiloxane).

The preparations according to the invention may advantageously also comprise one or more cosmetic active ingredients. Examples of preferred active ingredients include glycyrrhetic acid, urea, arctiin, alpha-lipoic acid, folic acid, phytoene, D-biotin, coenzyme Q10, alpha-glucosylrutin, carnitine, carnosine, caffeine, natural and/or synthetic isoflavonoids, glycerylglucose, creatine, creatinine, taurine, ß-alanine and licochalcone A.

According to the invention it further may be advantageous for the preparation to comprise one or more compounds selected from methylparaben, ethylparaben, propylparaben, piroctoneolamine, dehydracetic acid, organic acids such as, for example, sorbic acid, benzoic acid, salicylic acid and salts thereof, formaldehyde donors, organic halides, such as, for example, IPBC, ethyllauroyl arginates, quaternary compounds, such as, for example, benzalkonium chloride, cetrimonium chloride or bromide or benzethonium chloride, silver and silver compounds, 2-methylisothiazol-3(2H)-one and phenoxyethanol. Preparations comprising one or more compounds selected from ethanol, propylene glycol, butylene glycol, 2-methylpropane-1,3-diol, 1,2-pentanediol, 1,2-hexanediol, 1,2-octanediol, 1,2-decanediol, ethylhexylglycerol, glyceryl caprylates, hydroxamic acid, and chelating agents may also be advantageous.

The preparation according to the invention may advantageously be used for daycare or as a sunscreen, without being limited to these areas of application.

Comparative Experiments

The following experiments illustrate the effects obtainable according to the invention by way of example:

The following formulations were prepared and micrographs and photographs thereof were made.

| INCI | A | B | C |
|---|---|---|---|
| Cyclomethicone | 5.0 | 5.0 | 5.0 |
| C12-15 Alkyl Benzoate | 8.0 | 2.0 | 2.0 |
| Cetearyl Alcohol + PEG-40 Castor Oil + Sodium Cetearyl Sulfate | 3.0 | 3.0 | 3.0 |
| Sorbitan Stearate | 1.0 | 1.0 | 1.0 |
| Glyceryl Stearate SE | 1.0 | 1.0 | 1.0 |
| Glycerin | 5.0 | 5.0 | 5.0 |
| Titanium Dioxide + Methylhydrogenpolysiloxane | 23.7 | 23.7 | 23.7 |
| Ethylhexyl Methoxycrylene | | 6.0 | |
| Octocrylene | | | 6.0 |
| Methylparaben | 0.3 | 0.3 | 0.3 |
| Phenoxyethanol | 0.5 | 0.5 | 0.5 |
| Methylisothiazolinone | 0.1 | 0.1 | 0.1 |
| Xanthan Gum | 0.4 | 0.4 | 0.4 |
| Aqua | 46.4 | 46.4 | 46.4 |
| Benzophenone-3 | 5.7 | 5.7 | 5.7 |

Figure 1B:
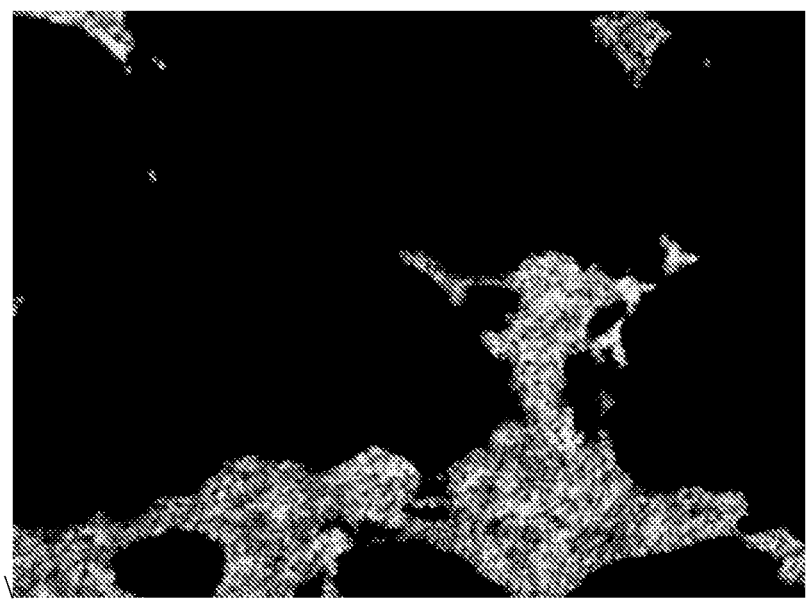
Figure 2A:
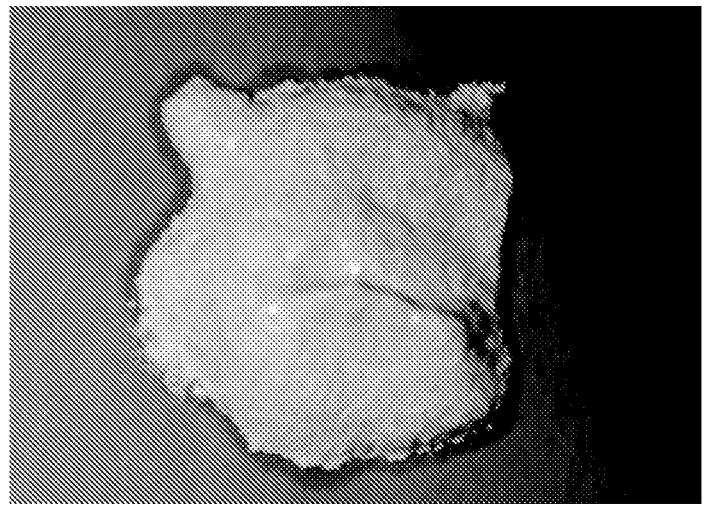
FIG. 2a and FIG. 2b are photographs of drops of a composition according to the invention and two comparative compositions.
Figure 2A:
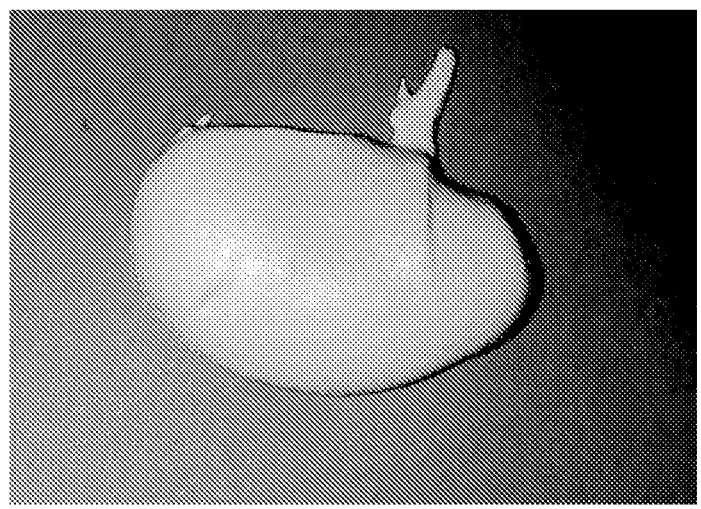
Figure 2B:
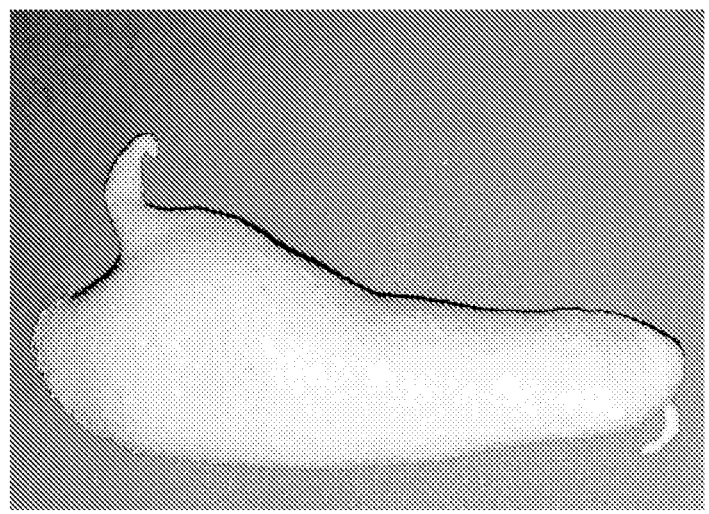

As can be seen from the micrographs shown in FIGS. 1a and 1b, the distribution of the titanium dioxide in the preparation according to the invention (B) containing ethylhexyl methoxycrylene is finer and more uniform than in the case of the preparations containing the same (additional) amount of octocrylene (C) or C12-15 alkylbenzoate (A). A better distribution of the titanium dioxide is usually an indicator of a higher stability of the formula. The photographs of FIGS. 2a and 2b also show a significantly more homogeneous structure of the surface in the case of ethylhexyl methoxycrylene (B).

Examples

The examples below are intended to illustrate the present invention. Unless stated otherwise, all quantitative data, fractions and percentages are based on the weight and the total amount or on the total weight of the preparations.

| INCI | 1 | 2 | 3 | 4 | 5 |
|---|---|---|---|---|---|
| Titanium Dioxide + Alumina, Triethoxy Caprylsilane | | | | | 23.7 |
| Zinc Oxide (nano) + Dimethicone | 15.0 | 24.0 | | 22.5 | |
| Titanium Dioxide + Simethicone | 10.0 | 6.0 | | 4.0 | |
| Titanium Dioxide + Methylhydrogenpolysiloxane | | | 23.7 | | |
| Ethylhexyl Methoxycrylene | 4.5 | 6.0 | 6.0 | 4.0 | 6.0 |

-continued

| INCI | 1 | 2 | 3 | 4 | 5 |
|---|---|---|---|---|---|
| Octocrylene | 4.5 | | | | |
| Ethylhexyl Salicylate | 4.5 | | | | |
| Ethylhexyl Methoxycinnamate + BHT | | 3.0 | | 3.0 | |
| Benzophenone-3 | | | 5.7 | | 5.7 |
| Piroctone Olamine | | 0.1 | | | |
| Cyclomethicone | 5.0 | 5.0 | 5.0 | 5.0 | 5.0 |
| C12-15 Alkyl Benzoate | 4.5 | 2.7 | 8.0 | 2.7 | 8.0 |
| Cetearyl Alcohol + PEG-40 Castor Oil + Sodium Cetearyl Sulfate | 3.0 | 3.0 | 3.0 | 3.0 | 3.0 |
| Sorbitan Stearate | 1.0 | 1.0 | 1.0 | 1.0 | 1.0 |
| Glyceryl Stearate SE | 1.0 | 1.0 | 1.0 | 1.0 | 1.0 |
| Glycerin | 5.0 | 5.0 | 5.0 | 5.0 | 5.0 |
| Lactic Acid | | 0.9 | | 0.9 | |
| Methylisothiazolinone | 0.1 | | 0.1 | 0.1 | 0.1 |
| Phenoxyethanol | | 0.5 | 0.5 | 0.5 | 0.5 |
| Methylparaben | | | 0.3 | 0.3 | 0.3 |
| Xanthan Gum | 0.4 | 0.4 | 0.4 | 0.4 | 0.4 |
| Aqua | Ad 100 | Ad 100 | Ad 100 | Ad 100 | Ad 100 |
| Sodium Lactate | | 1.9 | | 1.9 | |

| INCI | 6 | 7 | 8 | 9 | 10 |
|---|---|---|---|---|---|
| Titanium Dioxide + Alumina, Triethoxy Caprylsilane | | | | 16 | 22 |
| Zinc Oxide (nano) + Dimethicone | 15.0 | 24.0 | | 10 | 5 |
| Titanium Dioxide + Simethicone | 10.0 | 6.0 | 3 | 4.0 | |
| Titanium Dioxide + Methylhydrogenpolysiloxane | | | 22 | | |
| Ethylhexyl Methoxycrylene | 4.5 | 6.0 | 6.0 | 4.0 | 6.0 |
| Octocrylene | 4.5 | | | | |
| Ethylhexyl Salicylate | 4.5 | | | | 2 |
| Ethylhexyl Methoxycinnamate + BHT | | 3.0 | | 3.0 | |
| Benzophenone-3 | | | 7 | | 6 |
| Piroctone Olamine | | 0.1 | | 0.5 | |
| Cyclomethicone | 5.0 | 4 | 5.0 | 8 | 5.0 |
| C12-15 Alkyl Benzoate | 4.5 | 2.7 | 8.0 | 2.7 | 8.0 |
| Cetearyl Alcohol + PEG-40 Castor Oil + Sodium Cetearyl Sulfate | 3.0 | 3.0 | 2.6 | 3.0 | 3.0 |
| Sorbitan Stearate | 2 | 1.0 | 2.3 | 1.0 | 1.6 |
| Glyceryl Stearate SE | 1.0 | 1.0 | 1.0 | 1.0 | 1.0 |
| Glycerin | 4 | 5.0 | 5.0 | 8 | 16 |
| Lactic Acid | | 1 | | 1 | |
| Methylisothiazolinone | 0.1 | 0.0 | 0.1 | 0.1 | 0.1 |
| Phenoxyethanol | | 0.5 | 0.5 | 0.5 | 0.5 |
| Methylparaben | | | 0.3 | | 0.3 |
| Xanthan Gum | 0.4 | 0.4 | 0.4 | 0.4 | 0.4 |
| Aqua | Ad 100 | Ad 100 | Ad 100 | Ad 100 | Ad 100 |
| Sodium Lactate | | 2.5 | | 3 | |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic preparation, wherein the preparation is present as an emulsion and comprises, based on a total weight of the preparation:

(a) at least 4% by weight of a compound of formula (I):

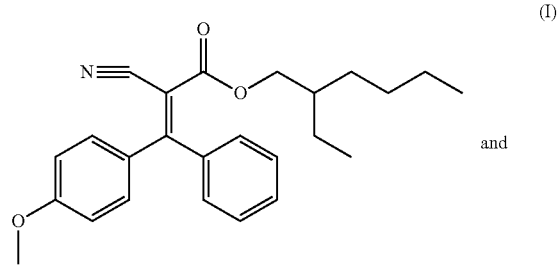 [SMILES: CCCCC(CC)COC(=O)/C(C#N)=C(\c1ccccc1)c1ccc(OC)cc1]

and (b) at least 20% by weight of (i) titanium dioxide having a surface coating consisting of one or more of sodium hexametaphosphate, sodium metaphosphate, iron oxide, aluminum stearate, stearic acid, lauric acid, dimethicone, methicone, methylhydrogenpolysiloxane, octyltrimethylsilane, triethoxycapryl silane, and/or of (ii) zinc oxide having a surface coating consisting of one or both of dimethicone and methicone.

2. The cosmetic preparation of claim 1, wherein the preparation is present as an O/W emulsion.

3. The cosmetic preparation of claim 2, wherein the preparation further comprises one or more O/W emulsifiers selected from glyceryl stearate citrate, glyceryl stearate, cetearyl glucosides, stearic acid and salts thereof, polyglyceryl-3 methylglycose distearate, ceteareth-20, PEG-40 stearate, PEG-100 stearate, sorbitan stearate, sodium cetearyl sulfate, cetearyl sulfosuccinate, sodium stearylglutamate, potassium cetylphosphate, dimethyl dioctadecylammonium chloride.

4. The cosmetic preparation of claim 1, wherein the preparation comprises (b)(i).

5. The cosmetic preparation of claim 1, wherein (b) comprises titanium dioxide having a surface coating consisting of one or more of sodium metaphosphate, stearic acid, lauric acid, dimethicone, methicone, methylhydrogenpolysiloxane, triethoxycapryl silane.

6. The cosmetic preparation of claim 1, wherein (b) comprises titanium dioxide having a surface coating consisting of one of sodium metaphosphate, iron oxide, stearic acid, lauric acid, dimethicone, methicone, methylhydrogenpolysiloxane, triethoxycapryl silane.

7. The cosmetic preparation of claim 1, wherein (b) comprises titanium dioxide having a surface coating consisting of one or more of sodium metaphosphate, iron oxide, stearic acid, lauric acid.

8. The cosmetic preparation of claim 1, wherein (b) comprises titanium dioxide having a surface coating consisting of methylhydrogenpolysiloxane.

9. The cosmetic preparation of claim 1, wherein the preparation comprises (b)(ii).

10. The cosmetic preparation of claim 1, wherein the preparation further comprises one or more UV filters which are different from (a) in total concentration of from 0.5% to 30% by weight, based on a total weight of the preparation.

11. The cosmetic preparation of claim 10, wherein the one or more UV filters comprise at least one of ethylhexyl salicylate, ethylhexyl methoxycinnamate, benzophenone-3.

12. A cosmetic preparation, wherein the preparation is present as an O/W emulsion and comprises, based on a total weight of the preparation:

(a) at least 4% by weight of a compound of formula (I):

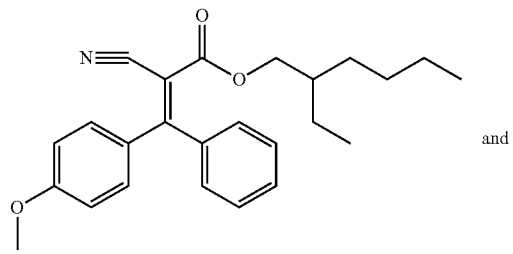

(I)

and (b) at least 20% by weight of (i) titanium dioxide having a surface coating consisting of methylhydrogenpolysiloxane, titanium dioxide having a surface coating consisting of stearic acid, caprylic/capric triglyceride and alumina, titanium dioxide having a surface coating consisting of dimethicone or simethicone, titanium dioxide having a surface coating consisting of iron oxide, titanium dioxide having a surface coating consisting of alumina and triethoxycaprylsilane and/or of (ii) zinc oxide having a surface coating consisting of one or both of dimethicone and methicone.

13. The cosmetic preparation of claim 12, wherein the preparation comprises at least 23% of (b)(i) and/or (b)(ii).

14. The cosmetic preparation of claim 12, wherein the preparation comprises titanium dioxide having a surface coating consisting of dimethicone.

15. The cosmetic preparation of claim 12, wherein the preparation comprises titanium dioxide having a surface coating consisting of simethicone.

16. The cosmetic preparation of claim 12, wherein the preparation comprises titanium dioxide having a surface coating consisting of stearic acid, caprylic/capric triglyceride and alumina.

17. The cosmetic preparation of claim 12, wherein the preparation comprises titanium dioxide having a surface coating consisting of alumina and triethoxycaprylsilane.

18. The cosmetic preparation of claim 12, wherein the preparation comprises zinc oxide having a surface coating consisting of one or both of dimethicone and methicone.

19. The cosmetic preparation of claim 12, wherein the preparation further comprises one or more UV filters which are different from (a) in total concentration of from 0.5% to 30% by weight, based on a total weight of the preparation.

20. The cosmetic preparation of claim 19, wherein the one or more UV filters comprise at least one of ethylhexyl salicylate, ethylhexyl methoxycinnamate, benzophenone-3.

* * * * *